US012691043B2

(12) United States Patent
Saito et al.

(10) Patent No.: US 12,691,043 B2
(45) Date of Patent: Jul. 28, 2026

(54) FRAGRANCE COMPOSITION

(71) Applicant: Kao Corporation, Tokyo (JP)

(72) Inventors: Akari Saito, Tokyo (JP); Hironori Mori, Tokyo (JP); Tsubasa Arai, Wakayama (JP)

(73) Assignee: Kao Corporation, Tokyo (JP)

( * ) Notice: Subject to any disclaimer, the term of this patent is extended or adjusted under 35 U.S.C. 154(b) by 455 days.

(21) Appl. No.: 18/255,931

(22) PCT Filed: Nov. 12, 2021

(86) PCT No.: PCT/JP2021/041663
§ 371 (c)(1),
(2) Date: Jun. 5, 2023

(87) PCT Pub. No.: WO2022/124003
PCT Pub. Date: Jun. 16, 2022

(65) Prior Publication Data
US 2024/0058239 A1 Feb. 22, 2024

(30) Foreign Application Priority Data
Dec. 7, 2020 (JP) ................................ 2020-202996

(51) Int. Cl.
*A61K 8/34* (2006.01)
*A61Q 13/00* (2006.01)

(52) U.S. Cl.
CPC ................ *A61K 8/34* (2013.01); *A61Q 13/00* (2013.01)

(58) Field of Classification Search
CPC ........ A61K 8/34; A61Q 13/00; C11B 9/0034; C11B 9/00; C07B 2200/09; C07C 2601/14; C07C 43/196
See application file for complete search history.

(56) References Cited

U.S. PATENT DOCUMENTS 5,194,423 A 3/1993 Koshino et al.
5,446,208 A 8/1995 Koshino et al.
(Continued)

FOREIGN PATENT DOCUMENTS

EP 0 467 290 A2 1/1992
EP 0 616 994 A2 9/1994
(Continued)

OTHER PUBLICATIONS

International Search Report issued Jan. 25, 2022 in PCT/JP2021/041663 filed on Nov. 12, 2021, 24 therein, 2 pages.
(Continued)

*Primary Examiner* — Jeffrey T. Palenik
(74) *Attorney, Agent, or Firm* — Oblon, McClelland, Maier & Neustadt, L.L.P.

(57) ABSTRACT

Compositions containing a cis isomer and a trans isomer, in which the cis isomer includes a compound represented by formula (Ia), a compound represented by formula (Ib), a compound represented by formula (IIa), and a compound represented by formula (IIb), the trans isomer includes a compound represented by formula (IIIa), a compound represented by formula (IIIb), a compound represented by formula (IVa), and a compound represented by formula (IVb), and a mass ratio of the cis isomer to the trans isomer [cis isomer:trans isomer] is 65:35 or more and 95:5 or less:

(Ia)

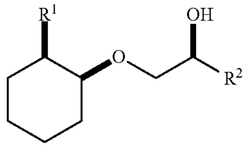

(IIa)

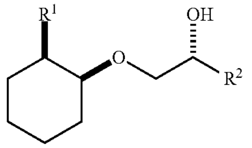

(IIIa)

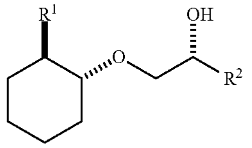

(IVa)

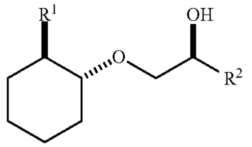

(Ib)

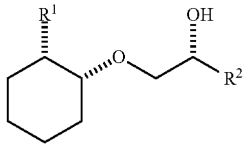

(IIb)

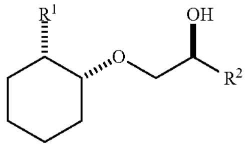

(IIIb)

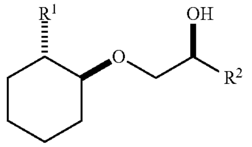

(Continued)

-continued

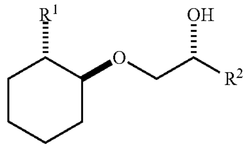
(IVb)

in which in the formulae (Ia), (Ib), (IIa), (IIb), (IIIa), (IIIb), (IVa), and (IVb), $R^1$ is an alkyl group having 1 or more and 5 or less of carbon atoms, and $R^2$ is a hydrogen atom or an alkyl group having 1 or more and 4 or less of carbon atoms, are useful as fragrances.

17 Claims, No Drawings

(56) References Cited

U.S. PATENT DOCUMENTS

| | | | |
|---|---|---|---|
| 2010/0130397 | A1 | 5/2010 | Reckziegel et al. |
| 2012/0059177 | A1 | 3/2012 | Gralla et al. |
| 2013/0230476 | A1 | 9/2013 | Pelzer et al. |
| 2014/0350306 | A1 | 11/2014 | Arai et al. |
| 2014/0378713 | A1 | 12/2014 | Arai et al. |
| 2017/0292084 | A1 | 10/2017 | Stork et al. |

FOREIGN PATENT DOCUMENTS

| | | | |
|---|---|---|---|
| JP | 4-217937 | A | 8/1992 |
| JP | 4-327553 | A | 11/1992 |
| JP | 5-339188 | A | 12/1993 |
| JP | 6-263677 | A | 9/1994 |
| JP | 8-27056 | A | 1/1996 |
| JP | 2008-514673 | A | 5/2008 |
| JP | 2012-527419 | A | 11/2012 |
| JP | 2013-151481 | A | 8/2013 |
| JP | 2013-151482 | A | 8/2013 |
| JP | 2013-151483 | A | 8/2013 |
| JP | 2014-503609 | A | 2/2014 |
| JP | 2017-530126 | A | 10/2017 |
| WO | WO 2013/099858 | A1 | 7/2013 |

OTHER PUBLICATIONS

Margot, C. et al., “Amber-Woody Scent: Alcohols with Divergent Structure Present Common Olfactory Characteristics and Sharp Enantiomer Differentiation”, Helvetica Chimica Acta, (2004), vol. 87, No. 10, pp. 2662-2684.

Extended European Search Report issued Sep. 16, 2024 in European Patent Application No. 21903107.7, 8 pgs.

European Office Action issued May 6, 2025 in European Patent Application No. 21903107.7, 5 pages.

FRAGRANCE COMPOSITION

CROSS REFERENCE TO RELATED APPLICATIONS

This application is a National Stage entry under 35 U.S.C. § 371 of PCT/JP2021/041663, filed on Nov. 12, 2021, and claims priority to Japanese Patent Application No. 2020-202996, filed on Dec. 7, 2020. The entire contents of both are incorporated herein by reference.

TECHNICAL FIELD

The present invention relates to a fragrance composition.

BACKGROUND ART

An α-(2-alkylcyclohexyloxy)-β-alkanol, especially 1-(2-t-butylcyclohexyloxy)-2-alkanol, is a useful fragrance material having a woody amber scent and excellent longevity while being produced at low costs (JP H04-217937 A).

For example, 1-(2-t-butylcyclohexyloxy)-2-butanol, widely known as Amber Core, is a fragrance having a woody-amber note (a fresh cypress scent) and high longevity.

Amber Core is a mixture of cis and trans isomers of 1-(2-t-butylcyclohexyloxy)-2-butanol (the mass ratio of the cis isomer to the trans isomer, cis isomer:trans isomer=1:0.5 to 1.0). Of these, the trans isomer has a particularly strong woody-amber note. The terms "cis" and "trans" mean that the functional groups attached to cyclohexane are "cis" and "trans", respectively. The cis and trans isomers of Amber Core specifically include the following stereo structures.

[Chemical Formula 1]
Amber Core

Cis isomer

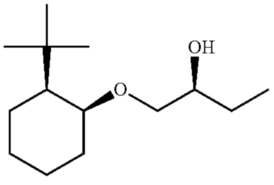 [SMILES: CC[C@H](O)CO[C@H]1CCCC[C@H]1C(C)(C)C]

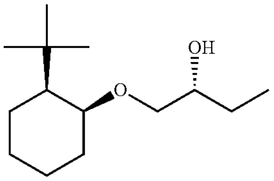 [SMILES: CC[C@@H](O)CO[C@H]1CCCC[C@H]1C(C)(C)C]

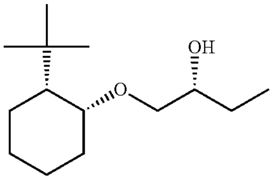 [SMILES: CC[C@@H](O)CO[C@@H]1CCCC[C@@H]1C(C)(C)C]

-continued

[Chemical Formula 1]
Amber Core

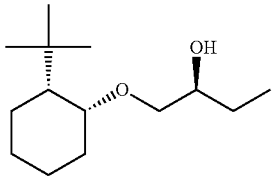 [SMILES: CC[C@H](O)CO[C@@H]1CCCC[C@@H]1C(C)(C)C]

Trans isomer

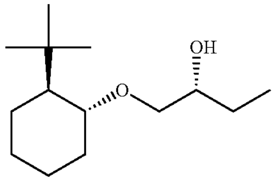 [SMILES: CC[C@@H](O)CO[C@@H]1CCCC[C@H]1C(C)(C)C]

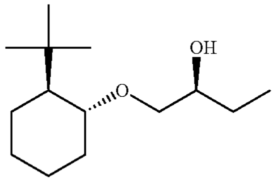 [SMILES: CC[C@H](O)CO[C@@H]1CCCC[C@H]1C(C)(C)C]

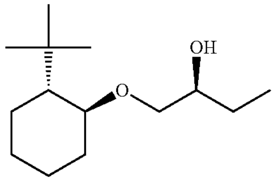 [SMILES: CC[C@H](O)CO[C@H]1CCCC[C@@H]1C(C)(C)C]

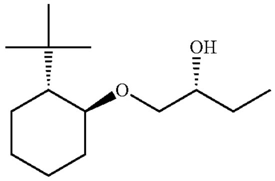 [SMILES: CC[C@@H](O)CO[C@H]1CCCC[C@@H]1C(C)(C)C]

DISCLOSURE OF INVENTION

The present invention provides a fragrance composition containing a cis isomer and a trans isomer,

- wherein the cis isomer includes a compound represented by formula (Ia), a compound represented by formula (Ib), a compound represented by formula (IIa), and a compound represented by formula (IIb),
- the trans isomer includes a compound represented by formula (IIIa), a compound represented by formula (IIIb), a compound represented by formula (IVa), and a compound represented by formula (IVb), and
- a mass ratio of the cis isomer to the trans isomer[cis isomer:trans isomer] is 65:35 or more and 95:5 or less.

[Chemical Formula 2]

(Ia)

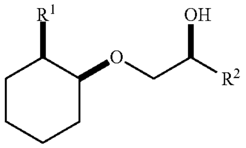

(IIa)

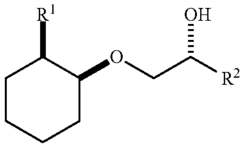

(IIIa)

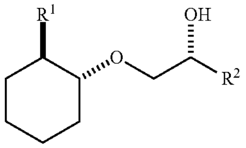

(IVa)

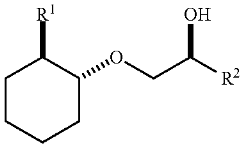

(Ib)

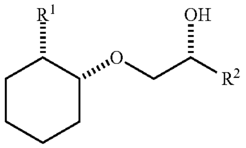

(IIb)

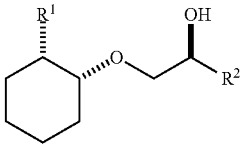

(IIIb)

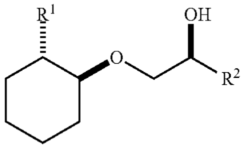

(IVb)

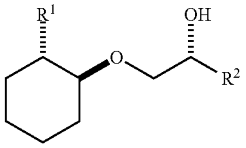

In the formulae (Ia), (Ib), (IIa), (IIb), (IIIa), (IIIb), (IVa), and (IVb), $R^1$ is an alkyl group having 1 or more and 5 or less of carbon atoms, and $R^2$ is a hydrogen atom or an alkyl group having 1 or more and 4 or less of carbon atoms.

DETAILED DESCRIPTION OF INVENTION

The present invention features the cis isomer of α-(2-alkylcyclohexyloxy)-β-alkanol that has not received attention in Amber Core, and it is an object of the present invention to provide a novel fragrance composition containing the same.

The present inventors have surprisingly found that a woody soft and fresh impression can be perceived in a fragrance composition containing the trans and cis isomers of α-(2-alkylcyclohexyloxy)-β-alkanol when the cis isomer ratio is preponderant, specifically, the mass ratio of the cis isomer to the trans isomer [cis isomer:trans isomer] is 65:35 or more and 95:5 or less. This impression is new and different from that of Amber Core. The present inventors have also found that by blending the fragrance composition as a fragrance material with other components, a sparkling zesty impression of a citrus top note is produced, and green and woody nuances are added together with a floral scent, giving a natural floral feeling like being in a flower shop, and thus new impressions are unexceptionally created. The fragrance composition of the present invention was accomplished based on the above finding.

The present invention is directed to a fragrance composition containing a cis isomer and a trans isomer, wherein the cis isomer includes a compound represented by formula (Ia), a compound represented by formula (Ib), a compound represented by formula (IIa), and a compound represented by formula (IIb), the trans isomer includes a compound represented by formula (IIIa), a compound represented by formula (IIIb), a compound represented by formula (IVa), and a compound represented by formula (IVb), and a mass ratio of the cis isomer to the trans isomer [cis isomer:trans isomer] is 65:35 or more and 95:5 or less. The compound represented by formula (Ia), the compound represented by formula (Ib), the compound represented by formula (IIa), and the compound represented by formula (IIb) are the cis isomer of α-(2-alkylcyclohexyloxy)-β-alkanol, whereas the compound represented by formula (IIIa), the compound represented by formula (IIIb), the compound represented by formula (IVa), and the compound represented by formula (IVb) are the trans isomer of α-(2-alkylcyclohexyloxy)-β-alkanol.

[Chemical Formula 3]

Cis isomer

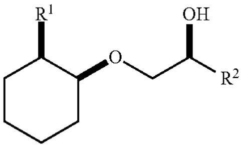

(Ia)

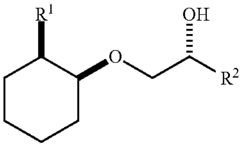

(IIa)

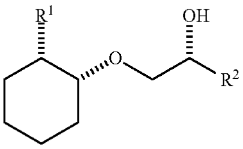

(Ib)

-continued

[Chemical Formula 3]

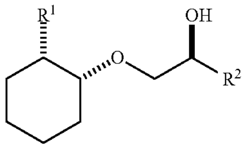

(IIb)

Trans isomer

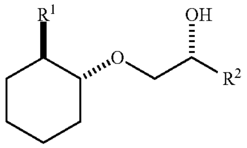

(IIIa)

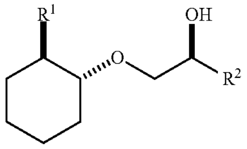

(IVa)

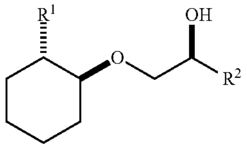

(IIIb)

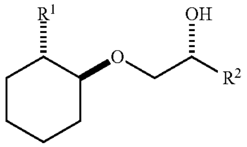

(IVb)

In the formulae (Ia), (Ib), (Ia), (IIb), (IIIa), (IIIb), (IVa), and (IVb), $R^1$ is an alkyl group having 1 or more and 5 or less of carbon atoms, and $R^2$ is a hydrogen atom or an alkyl group having 1 or more and 4 or less of carbon atoms.

The fragrance composition of the present invention contains a specific ratio of the cis isomer of α-(2-alkylcyclohexyloxy)-β-alkanol, and thus being excellent in harmony with various other fragrances and capable of creating a distinctive fragrance effect when blended.

As described above, the present invention is directed to a fragrance composition containing a cis isomer and a trans isomer, wherein the cis isomer includes a compound represented by formula (Ia), a compound represented by formula (Ib), a compound represented by formula (IIa), and a compound represented by formula (IIb), the trans isomer includes a compound represented by formula (IIIa), a compound represented by formula (IIIb), a compound represented by formula (IVa), and a compound represented by formula (IVb), and a mass ratio of the cis isomer to the trans isomer [cis isomer:trans isomer] is 65:35 or more and 95:5 or less from the viewpoint of usability of the scent as a fragrance material for giving a woody soft and fresh impression, a natural richness, and longevity in a good balance. The mass ratio of the cis isomer to the trans isomer [cis isomer:trans isomer] is preferably 68:32 or more and 90:10 or less, more preferably 68:32 or more and 85:15 or less, and further preferably 68:32 or more and 75:25 or less, from the viewpoint of usability of the scent as a fragrance material for giving a woody soft and fresh impression, a natural richness, and longevity in a good balance.

The mass ratio of the cis isomer to the trans isomer [cis isomer:trans isomer] is 65:35 or more, preferably 68:32 or more, more preferably 82:18 or more, and further preferably 85:15 or more, from the viewpoint of giving a woody soft and fresh impression.

The mass ratio of the cis isomer to the trans isomer [cis isomer:trans isomer] is 95:5 or less, preferably 90:10 or less, more preferably 85:15 or less, further preferably 78:22 or less, and still further preferably 75:25 or less, from the viewpoint of giving a natural richness, intensity, and longevity.

Therefore, the mass ratio of the cis isomer to the trans isomer [cis isomer:trans isomer] is preferably 82:18 or more and 95:5 or less, more preferably 82:18 or more and 90:10 or less, and further preferably 85:15 or more and 90:10 or less, from the viewpoint of giving a woody soft and fresh impression.

The mass ratio of the cis isomer to the trans isomer [cis isomer:trans isomer] is preferably 65:35 or more and 78:22 or less, more preferably 68:32 or more and 78:22 or less, and further preferably 68:32 or more and 75:25 or less, from the viewpoint of giving a natural richness, intensity, and longevity.

[Chemical Formula 4]

Cis isomer

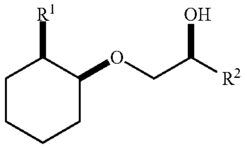

(Ia)

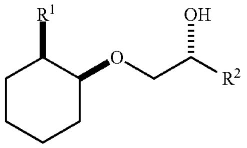

(IIa)

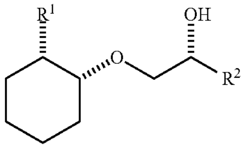

(Ib)

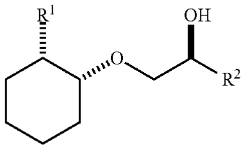

(IIb)

Trans isomer

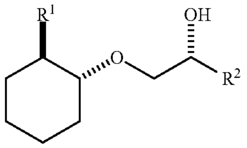

(IIIa)

-continued

[Chemical Formula 4]

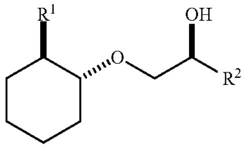

(IVa)

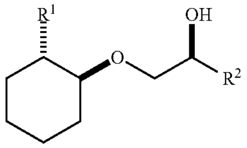

(IIIb)

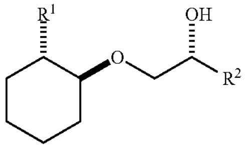

(IVb)

In the formulae (Ia), (Ib), (IIa), (IIb), (IIIa), (IIIb), (IVa), and (IVb), $R^1$ is an alkyl group having 1 or more and 5 or less of carbon atoms, and $R^2$ is a hydrogen atom or an alkyl group having 1 or more and 4 or less of carbon atoms.

In the present invention, the cis isomer includes the compound represented by formula (Ia), the compound represented by formula (Ib), the compound represented by formula (IIa), and the compound represented by formula (IIb). In the cis isomer, a mass ratio of a sum of the compound represented by formula (Ia) and the compound represented by formula (Ib) to a sum of the compound represented by formula (IIa) and the compound represented by formula (IIb) [the sum of the compound represented by formula (Ia) and the compound represented by formula (Ib): the sum of the compound represented by formula (IIa) and the compound represented by formula (IIb)] (also referred to as a "cis isomer ratio") is preferably 55:45 or more and 68:32 or less, more preferably 55.5:44.5 or more and 66:34 or less, and further preferably 56:44 or more and 62:38 or less, from the viewpoint of producing a sparkling zesty impression of a citrus top note and adding green and woody nuances together with a floral scent, giving a natural floral feeling like being in a flower shop.

In the fragrance composition of the present invention, for example, the mass concentration of the cis isomer is preferably 65% by mass or more, more preferably 66% by mass or more, further preferably 67% by mass or more, still further preferably 68% by mass or more, and even further preferably 69% by mass or more from the viewpoint of giving a woody soft and fresh impression and a natural richness, and the mass concentration of the cis isomer is preferably 95% by mass or less, more preferably 85% by mass or less, further preferably 80% by mass or less, and even further preferably 75% by mass or less from the viewpoint of giving a natural richness, intensity, and longevity. The fragrance composition satisfying the above proportion is excellent in harmony with various other fragrances and can create a distinctive fragrance effect when blended.

The compound represented by formula (Ia), the compound represented by formula (Ib), the compound represented by formula (IIa), and the compound represented by formula (IIb), the compound represented by formula (IIIa), the compound represented by formula (IIIb), the compound represented by formula (IVa), and the compound represented by formula (IVb) may be produced by a conventionally known method, for example, the method described in JP H04-217937 A.

Alternatively, the compound represented by formula (Ia), the compound represented by formula (Ib), the compound represented by formula (IIa), and the compound represented by formula (IIb), the compound represented by formula (IIIa), the compound represented by formula (IIIb), the compound represented by formula (IVa), and the compound represented by formula (IVb) may be produced, for example, by the following method.

[Chemical Formula 5]

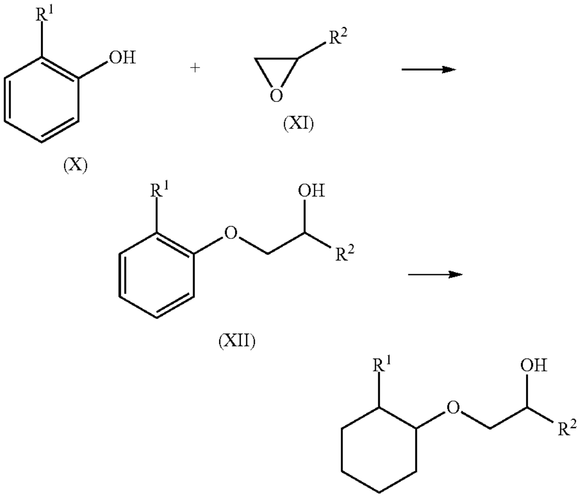

(X) (XI) (XII) (XIII)

In the formulae (X), (XI), (XII), and (XIII) above, $R^1$ is an alkyl group having 1 or more and 5 or less of carbon atoms, and $R^2$ is a hydrogen atom or an alkyl group having 1 or more and 4 or less of carbon atoms.

The compound of formula (X) and the compound of formula (XI) are heated in the presence of a base (e.g., sodium hydroxide) to yield the compound of formula (XII). The compound of formula (XII) is hydrogenated in the presence of hydrogen and a catalyst (e.g., a palladium catalyst) to yield the compound of formula (XIII). The compound of formula (XIII) thus obtained is a mixture of the cis isomer and the trans isomer, the cis isomer including the compound represented by formula (Ia), the compound represented by formula (Ib), the compound represented by formula (IIa), and the compound represented by formula (IIb), and the trans isomer including the compound represented by formula (IIIa), the compound represented by formula (IIIb), the compound represented by formula (IVa), and the compound represented by formula (IVb). The compound of formula (XIII) thus obtained can be separated by distillation or column chromatography to isolate the cis isomer or trans isomer of high purity. As needed, a mixture containing the cis and trans isomers at a desired ratio can be obtained by mixing the compound of formula (XIII) (the mixture of the cis and trans isomers at a specific ratio), with the cis isomer of high purity (including the compound represented by formula (Ia), the compound represented by formula (Ib), the compound represented by formula (IIa), and the compound represented by formula (IIb)) or the trans isomer of high purity (including the compound represented by formula (IIIa), the compound represented by formula (IIIb), the compound represented by formula (IVa), and the compound represented by formula (IVb).

[Chemical Formula 6]

(Ia)

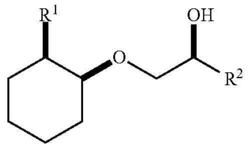

(IIa)

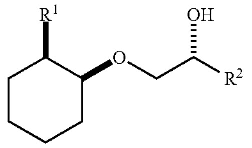

(IIIa)

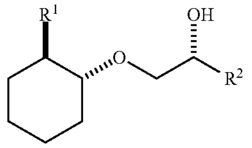

(IVa)

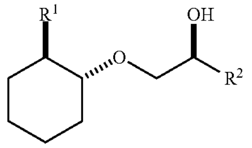

(Ib)

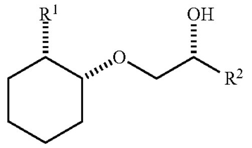

(IIb)

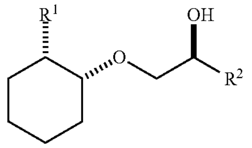

(IIIb)

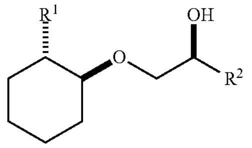

(IVb)

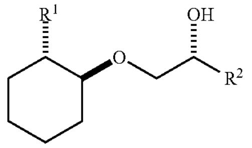

In the formulae (Ia), (Ib), (IIa), (IIb), (IIIa), (IIIb), (IVa), and (IVb), $R^1$ is an alkyl group having 1 or more and 5 or less of carbon atoms, and $R^2$ is a hydrogen atom or an alkyl group having 1 or more and 4 or less of carbon atoms.

In the formulae (Ia), (Ib), (IIa), (IIb), (IIIa), (IIIb), (IVa), and (IVb), $R^1$ is preferably an alkyl group having 1 or more and 4 or less of carbon atoms, more preferably an alkyl group having 3 or more and 4 or less of carbon atoms, and further preferably a t-butyl group. $R^2$ is preferably a methyl group or an ethyl group.

The composition of the present invention contains the cis and trans isomers at a specific ratio, and thus being excellent in harmony with various other fragrances and capable of creating a distinctive fragrance effect when blended. Moreover, the fragrance composition of the present invention can be combined with fragrances other than the cis and trans isomers, such as commonly used fragrance components and a formulated fragrance material having a desired composition. By being combined with the fragrances other than the cis and trans isomers, the fragrance composition of the present invention can produce, for example, a sparkling zesty impression of a top note, and add green and woody nuances together with a floral scent, giving a natural floral feeling like being in a flower shop. In other words, the fragrance composition of the present invention is preferably a composition further containing fragrances other than the group consisting of the cis and trans isomers.

In the composition of the present invention, examples of the other fragrances that can be used in combination with the cis and trans isomers include fragrance components of alcohols, hydrocarbons, phenols, esters, carbonates, aldehydes, ketones, acetals, ethers, carboxylic acids, lactones, nitriles, Schiff bases, and natural essential oils and natural extracts (excluding the cis and trans isomers described above).

Among them, alcohols, phenols, esters, carbonates, aldehydes, ketones, acetals, ethers, lactones, nitriles, natural essential oils, and natural extracts are preferred.

In the present specification, the "plural notation" of each fragrance denotes a single compound or a mixture of two or more compounds.

Examples of the alcohols include aliphatic alcohols, terpene-based alcohols, aromatic alcohols, and other alcohols. Among them, aliphatic alcohols are preferred.

Examples of the terpene-based alcohols include limonene, linalool, citronellol, geraniol, nerol, terpineol, a-terpineol, dihydromyrcenol, farnesol, nerolidol, cedrol, menthol, borneol, and Florol® (4-methyl-2-(2-methylpropyl) oxan-4-ol) (Florosa).

Examples of the aromatic alcohols include phenylethyl alcohol, benzyl alcohol, dimethyl benzyl carbinol, phenylethyl dimethyl carbinol, and phenyl hexanol.

Examples of the aliphatic alcohols include cis-3-hexenol, 1-(2,2,6-trimethylcyclohexyl)-3-hexanol, Sandalmysore Core (trade name of Kao Corporation, 2-methyl-4-(2,2,3-trimethyl-3-cyclopenten-1-yl)-2-buten-1-ol), Magnol (trade name of Kao Corporation, a mixture containing ethyl norbornyl cyclohexanol as a main component), Undecavertol (trade name of Givaudan, 4-methyl-3-decen-5-ol), and isobornyl cyclohexanol.

Examples of the other alcohols include glycols such as dipropylene glycol, and Florosa (trade name of Givaudan, chemical name: 4-methyl-2-(2-methylpropyl)tetrahydro-2H-4-pyranol).

Examples of the hydrocarbons include limonene, α-pinene, β-pinene, terpinene, cedrene, longifolene, and valencene.

Examples of the phenols include guaiacol, eugenol, dihydroeugenol, isoeugenol, thymol, para-cresol, vanillin, and ethyl vanillin.

Examples of the esters include aliphatic carboxylic acid ester, aromatic carboxylic acid ester, and other carboxylic acid esters.

Examples of aliphatic carboxylic acids that form aliphatic carboxylic acid ester include linear and branched carboxylic acids having 1 to 18 carbon atoms. Among them, carboxylic acids having 1 to 6 carbon atoms such as formic acid, acetic acid, and propionic acid are important, and acetic acid is particularly important. Examples of aromatic carboxylic acids that form aromatic carboxylic acid ester include benzoic acid, anisic acid, phenylacetic acid, cinnamic acid, salicylic acid, and anthranilic acid. Examples of alcohols that form aliphatic and aromatic esters include linear and branched aliphatic alcohols having 1 to 5 carbon atoms and the above-mentioned fragrance component alcohols.

Examples of the formate include linalyl formate, citronellyl formate, and geranyl formate.

Examples of the acetate include ethyl acetate, isoamyl acetate (isopentyl acetate), benzyl acetate, hexyl acetate, cis-3-hexenyl acetate, linalyl acetate, citronellyl acetate, geranyl acetate, neryl acetate, terpinyl acetate, nopyl acetate, bornyl acetate, isobornyl acetate, acetyl eugenol, acetyl isoeugenol, o-tert-butylcyclohexyl acetate, p-tert-butylcyclohexyl acetate, tricyclodecenyl acetate, benzyl acetate, phenylethyl acetate, styralyl acetate, cinnamyl acetate, dimethylbenzylcarbinyl acetate, phenylethyl phenyl acetate, 3-pentyltetrahydropyran-4-yl acetate, and para-cresyl phenyl acetate.

Examples of the propionate include citronellyl propionate, tricyclodecenyl propionate, allylcyclohexyl propionate, ethyl 2-cyclohexyl propionate, benzyl propionate, and styralyl propionate.

Examples of butyrate include citronellyl butyrate, dimethylbenzylcarbinyl n-butyrate, and tricyclodecenyl isobutyrate.

Examples of valerate include methyl valerate, ethyl valerate, butyl valerate, amyl valerate, benzyl valerate, and phenylethyl valerate. Examples of the hexanoate include methyl hexanoate, ethyl hexanoate, allyl hexanoate, linalyl hexanoate, and citronellyl hexanoate.

Examples of heptanoate include methyl heptanoate and allyl heptanoate.

Examples of nonenoate include methyl 2-nonenoate, ethyl 2-nonenoate, and ethyl 3-nonenoate.

Examples of the benzoate include methyl benzoate, benzyl benzoate, and 3,6-dimethyl benzoate.

Examples of the cinnamate include methyl cinnamate and benzyl cinnamate.

Examples of the salicylate include methyl salicylate, n-hexyl salicylate, cis-3-hexenyl salicylate, cyclohexyl salicylate, and benzyl salicylate.

Examples of brassylate include ethylene brassylate.

Examples of tiglate include geranyl tiglate, 1-hexyl tiglate, and cis-3-hexenyl tiglate.

Examples of jasmonate include methyl jasmonate and methyl dihydrojasmonate.

Examples of glycidate include methyl 2,4-dihydroxyethylmethylphenyl glycidate and 4-methylphenylethyl glycidate.

Examples of anthranilate include methyl anthranilate, ethyl anthranilate, and dimethyl anthranilate.

Examples of glycolate include allyl cyclohexyl glycolate.

Examples of other esters include Ethyl Safranate (trade name of Givaudan, ethyl dihydrocyclo geranate), Poirenate (trade name of Kao Corporation, ethyl-2-cyclohexyl propionate), Fruitate (trade name of Kao Corporation, ethyl tricyclo [5.2.1.$0^{2,6}$]decan-2-carboxylate), methyl jasmonate, MDJ (trade name of Kao Corporation, methyl dihydrojasmonate, methyl (2-pentyl-3-oxocyclopentyl)acetate), and Cyclohexyl Salicylate (trade name of Kao Corporation).

Examples of the carbonates include Liffarome (trade name of IFF, cis-3-hexenyl methyl carbonate), Jasmacyclat (trade name of Kao Corporation, methyl cyclooctyl carbonate), and Floramat (trade name of Kao Corporation, ethyl-2-t-butylcyclohexyl carbonate).

Examples of the aldehydes include n-octanal, n-nonanal, n-decanal, n-dodecanal, 2-methyl undecanal, 10-undecenal, citronellal, citral, hydroxycitronellal, Triplal (trade name of IFF, 2,4-dimethyl-3-cyclohexene-1-carboxaldehyde), Cyclovertal (trade name of Kao Corporation, dimethyl-3-cyclohexenyl-1-carboxaldehyde), benzaldehyde, phenylacetaldehyde, phenylpropylaldehyde, cinnamaldehyde, dimethyltetrahydrobenzaldehyde, Bourgeonal (trade name of Givaudan, 3-(4-tert-butylphenyl)propanal), Lyral (trade name of IFF, hydroxy myrac aldehyde), Pollenal II (trade name of Kao Corporation, 2-cyclohexyl propanal), Lilial (trade name of Givaudan, p-tert-butyl-α-methyl hydrocinnamaldehyde), p-isopropyl-α-methyl hydrocinnamaldehyde, Floralozone (trade name of IFF, 3-(o-(and p-)ethylphenyl)-2,2-dimethylpropionaldehyde, α-amyl cinnamaldehyde, α-hexyl cinnamaldehyde, heliotropin, Helional (trade name of IFF, alpha-methyl-1,3-benzodioxole-5-propanal), and Canthoxal (trade name of IFF, 2-methyl-3-(para-methoxyphenyl)propanal).

Examples of the ketones include methyl heptenone, dimethyl octenone, 3-octanone, hexylcyclopentanone, dihydrojasmone, Veloutone (trade name of Firmenich, 2,2,5-trimethyl-5-pentylcyclopentanone), Nectaryl (trade name of Givaudan, 2-(2-(4-methyl-3-cyclohexen-1-yl)propyl)cyclopentanone), ionone, β-ionone, methylionone, methylionone-G, γ-methylionone, damascone, α-damascone, β-damascone, δ-damascone, Isodamascone (trade name of Symrise AG, 1-(2,4,4-trimethyl-2-cyclohexyl)-trans-2-butanone), damascenone, Dynascone (trade name of Firmenich, 1-(5,5-dimethyl-1-cyclohexen-1-yl)-4-penten-1-one), irone, Cashmeran (trade name of IFF, 1,2,3,5,6,7-hexahydro-1,1,2,3,3-pentamethyl-4H-inden-4-one), Iso E Super (trade name of IFF, 1-(1,2,3,4,5,6,7,8-octahydro-2,3,8,8-tetramethyl-2-naphthalenyl)-ethan-1-one), Calone (trade name of Firmenich, 7-methyl-3,4-dihydro-2H-benzodioxepin-3-one), carvone, menthone, acetyl cedrene, isolongifolanone, nootkatone, benzyl acetone, raspberry ketone, benzophenone, Tonalid (trade name of PFW, 6-acetyl-1,1,2,4,4,7-hexamethyl tetrahydronaphthalene), β-methyl naphthyl ketone, ethyl maltol, camphor, muscone, Muscenone (trade name of Firmenich, 3-methyl-5-cyclopentadecen-1-one), civetone, Globanone (trade name of Symrise AG, 8-cyclohexadecenone), methyl nonyl ketone, and cis-jasmone, para-amylcyclohexanone (4-pentylcyclohexanone). Among them, ionone, damascenone, Iso E Super, or γ-methylionone is preferred from the viewpoint of emphasizing floral sweetness by blending with other fragrances.

Examples of the acetals include acetaldehyde ethylphenylpropyl acetal, citral diethyl acetal, phenylacetaldehyde glyceryl acetal, ethyl acetoacetate ethylene glycol acetal, Boisambrene Forte (trade name of Kao Corporation), and Troenan (trade name of Kao Corporation).

Examples of the ethers include ethyl linalool, cedryl methyl ether, estragole, anethole, β-naphthyl methyl ether, β-naphthyl ethyl ether, limonene oxide, rose oxide, nerol oxide, 1,8-cineole, rose furan, Ambroxan (trade name of Kao Corporation, [3aR-(3aα, 5aβ, 9aα, 9bβ)]-dodecahydro-3a,6,6,9a-tetramethyl naptho[2,1-b]furan), Herbavert (trade name of Kao Corporation, 3,3,5-trimethylcyclohexyl ethyl ether), Galaxolide (trade name of IFF, hexamethylhexahydrocyclopentabenzopyran), and phenylacetaldehyde dimethyl acetal.

Examples of the carboxylic acids include benzoic acid, phenylacetic acid, cinnamic acid, hydrocinnamic acid, butyric acid, and 2-hexenoic acid.

Examples of the lactones include ambrettolide, γ-decalactone, δ-decalactone, γ-valerolactone, γ-nonalactone, γ-undecalactone, δ-hexalactone, γ-jasmolactone, whisky lactone, coumarin, cyclopentadecanolide, cyclohexadecanolide, 11-oxahexadecanolide, and butylidenephthalide.

Examples of the nitriles include tridecene-2-nitrile, geranyl nitrile, citronellyl nitrile, and dodecanenitrile.

Examples of the Schiff bases include aurantiol and ligantral.

Examples of the natural essential oils and natural extracts include orange, lemon, lime, bergamot, vanilla, mandarin, peppermint, spearmint, lavender, chamomile, rosemary, eucalyptus, sage, basil, rose, rockrose, geranium, jasmine, ylang ylang, anise, clove, ginger, nutmeg, cardamon, cedar, cypress, vetiver, patchouli, lemongrass, labdanum, grapefruit, and elemi oil.

Among these, the fragrance composition of the present invention preferably further contains at least one selected from a lime essential oil, limonene, and menthol, from the viewpoint of producing a sparkling zesty impression of a citrus top note.

Further, among these, the fragrance composition of the present invention preferably further contains at least one selected from Florol® (4-methyl-2-(2-methylpropyl)oxan-4-ol), hexyl acetate, and methyl dihydrojasmonate, from the viewpoint of adding green and woody nuances together with a floral scent, giving a natural floral feeling like being in a flower shop.

The content of the other fragrances may be determined appropriately depending on, e.g., the type of the formulated fragrance material as well as the type and intensity of intended scents, but the content of each of them in a composition containing the fragrance composition of the present invention is preferably 0.0001% by mass or more, more preferably 0.001% by mass or more, and preferably 99.99% by mass or less, more preferably 80% by mass or less. Furthermore, the total content of the other fragrances in the composition containing the fragrance composition of the present invention is preferably 5% by mass or more, more preferably 50% by mass or more, and preferably 99.99% by mass or less, and more preferably 99.95% by mass or less.

The fragrance composition of the present invention may contain a scentless oil as a base. Such an oil allows fragrance components to be mixed uniformly, is easily mixed into a product, and appropriately adjusts the intensity of the fragrance. Examples of the oil include polyhydric alcohols such as ethylene glycol, propylene glycol, butylene glycol, and dipropylene glycol; esters such as isopropyl myristate, dibutyl adipate, and diethyl sebacate; hydrocarbons such as liquid paraffin and squalane; and surfactants such as polyoxyethylene alkyl ether and sorbitan fatty acid ester.

Among them, the oil is preferably polyhydric alcohol or ester, and more preferably dipropylene glycol or isopropyl myristate, from the viewpoint of the solubility of all the fragrance components. The content of the oil in the fragrance composition is preferably 0.01% by mass or more, more preferably 1% by mass or more, and further preferably 5% by mass or more, and preferably 95% by mass or less, more preferably 90% by mass or less, and further preferably 80% by mass or less.

The present invention further provides a cleaning composition containing the fragrance composition of the present invention, a cosmetic containing the fragrance composition of the present invention, and a textile-treating composition containing the fragrance composition of the present invention.

The cleaning composition of the present invention is preferably a body cleaning composition, a clothing cleaning composition, or a hard surface cleaning composition, more preferably a body cleaning composition or clothing cleaning composition, and further preferably a clothing cleaning composition.

Examples of the body cleaning composition include a skin cleaning composition, a hair cleaning composition, and a soap composition, and a skin cleaning composition is preferred.

Examples of the hard surface cleaning composition include an all-purpose cleaner and a dish cleaning composition.

The textile-treating composition of the present invention is preferably a softener composition.

The cosmetic of the present invention is preferably a perfume, a milky lotion, a skin lotion, or a sunscreen, and more preferably a perfume.

The cleaning composition of the present invention preferably contains an anionic surfactant in addition to the fragrance composition of the present invention, and may further contain a nonionic surfactant, a pH adjuster, a viscosity modifier, a solvent, an oil, a preservative, water, and the like.

The textile-treating composition of the present invention preferably contains a cationic surfactant in addition to the fragrance composition of the present invention, and may further contain a pH adjuster, a solvent, an oil, a preservative, water, and the like.

The perfume of the present invention may contain a solvent, water, and the like, in addition to the fragrance composition of the present invention.

The fragrance composition of the present invention containing the cis and trans isomers at a specific ratio gives a woody soft and fresh impression. Further, as described above, by blending the fragrance composition of the present invention as a fragrance material with other components, a sparkling zesty impression of a citrus top note is produced, and green and woody nuances are added together with a floral scent, giving a natural floral feeling like being in a flower shop, and thus new impressions are provided.

Therefore, the present invention is directed to a method for using the fragrance composition of the present invention containing the cis and trans isomers at a specific ratio as a fragrance-imparting component, specifically, a method for using the fragrance composition of the present invention as a fragrance-imparting component for a fragrance composition, a cleaning composition, a cosmetic, or a textile-treating composition. The cleaning composition is preferably a body cleaning composition, a clothing cleaning composition, or a hard surface cleaning composition, more preferably a body cleaning composition or clothing cleaning composition, and further preferably a clothing cleaning composition. Examples of the body cleaning composition include a skin cleaning composition, a hair cleaning composition, and a soap composition, and a skin cleaning composition is preferred. Examples of the hard surface cleaning composition include an all-purpose cleaner and a dish cleaning composition. The cosmetic is preferably a perfume. The textile treating composition is preferably a softener composition.

In the method of use, the amount of the fragrance composition of the present invention is preferably 0.00001% by mass or more, more preferably 0.0001% by mass or more, and preferably 0.01% by mass or less, and more preferably 0.001% by mass or less, with respect to the amount of the cleaning composition, cosmetic, or softener composition. Within the above amount, when the fragrance composition is blended with other components as a fragrance material, a sparkling zesty impression of a citrus top note is produced, and green and woody nuances are added together with a floral scent, giving a natural floral feeling like being in a flower shop, and thus new impressions are created.

In the method of use, the fragrance composition of the present invention may be blended with a scentless oil. The oil is the same as those in the description of the fragrance composition. In the method of use, the fragrance composition of the present invention may contain other fragrances, such as commonly used fragrance components and a formulated fragrance material having a desired composition. Such other fragrances are the same as those in the description of the fragrance composition.

The present invention includes the following aspects.

<1> A fragrance composition containing a cis isomer and a trans isomer, wherein the cis isomer includes a compound represented by formula (Ia), a compound represented by formula (Ib), a compound represented by formula (IIa), and a compound represented by formula (IIb), the trans isomer includes a compound represented by formula (IIIa), a compound represented by formula (IIIb), a compound represented by formula (IVa), and a compound represented by formula (IVb), and a mass ratio of the cis isomer to the trans isomer [cis isomer:trans isomer] is 65:35 or more and 95:5 or less.

[Chemical Formula 7]

(Ia)

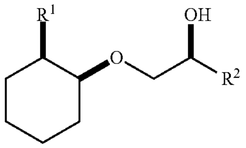

(IIa)

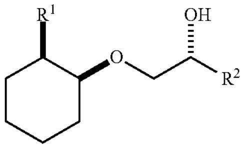

(IIIa)

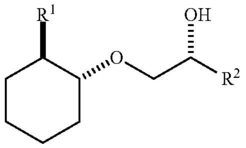

-continued (IVa)

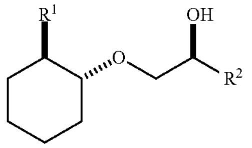

(Ib)

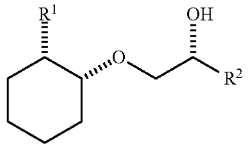

(IIb)

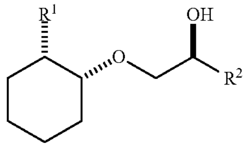

(IIIb)

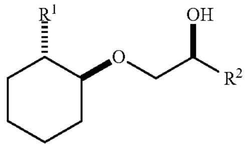

(IVb)

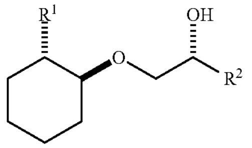

In the formulae (Ia), (Ib), (IIa), (IIb), (IIIa), (IIIb), (IVa), and (IVb), $R^1$ is an alkyl group having 1 or more and 5 or less of carbon atoms, and $R^2$ is a hydrogen atom or an alkyl group having 1 or more and 4 or less of carbon atoms.

<2> The fragrance composition according to <1>, wherein the mass ratio of the cis isomer to the trans isomer [cis isomer:trans isomer] is 68:32 or more and 90:10 or less.

<3> The fragrance composition according to <1> or <2>, wherein the mass ratio of the cis isomer to the trans isomer [cis isomer:trans isomer] is 68:32 or more and 85:15 or less.

<4> The fragrance composition according to any of <1> to <3>, wherein the mass ratio of the cis isomer to the trans isomer [cis isomer:trans isomer] is 68:32 or more and 75:25 or less.

<5> The fragrance composition according to any of <1> to <4>, wherein a mass concentration of the cis isomer in the fragrance composition is 65% by mass or more and 95% by mass or less.

<6> The fragrance composition according to any of <1> to <5>, wherein a mass concentration of the cis isomer in the fragrance composition is 66% by mass or more and 85% by mass or less.

<7> The fragrance composition according to any of <1> to <6>, wherein a mass concentration of the cis isomer in the fragrance composition is 67% by mass or more and 80% by mass or less.

<8> The fragrance composition according to any of <1> to <7>, wherein a mass concentration of the cis isomer in the fragrance composition is 68% by mass or more and 75% by mass or less.

<9> The fragrance composition according to any of <1> to <8>, wherein a mass ratio of a sum of the compound represented by formula (Ia) and the compound represented by formula (Ib) to a sum of the compound represented by formula (IIa) and the compound represented by formula (IIb) [the sum of the compound represented by formula (Ia) and the compound represented by formula (Ib): the sum of the compound represented by formula (IIa) and the compound represented by formula (IIb)] is 55:45 or more and 68:32 or less.

<10> The fragrance composition according to any of <1> to <9>, wherein a mass ratio of a sum of the compound represented by formula (Ia) and the compound represented by formula (Ib) to a sum of the compound represented by formula (IIa) and the compound represented by formula (IIb) is 55.5:44.5 or more and 66:34 or less.

<11> The fragrance composition according to any of <1> to <10>, wherein a mass ratio of a sum of the compound represented by formula (Ia) and the compound represented by formula (Ib) to a sum of the compound represented by formula (IIa) and the compound represented by formula (IIb) is 56:44 or more and 62:38 or less.

<12> The fragrance composition according to any of <1> to <11>, wherein the mass ratio of the cis isomer to the trans isomer [cis isomer:trans isomer] is 65:35 or more and 78:22 or less.

<13> The fragrance composition according to any of <1> to <12>, wherein the mass ratio of the cis isomer to the trans isomer [cis isomer:trans isomer] is 68:32 or more and 78:22 or less.

<14> The fragrance composition according to any of <1> to <13>, wherein the mass ratio of the cis isomer to the trans isomer [cis isomer:trans isomer] is 68:32 or more and 75:25 or less.

<15> The fragrance composition according to any of <1> to <14>, wherein the mass ratio of the cis isomer to the trans isomer [cis isomer:trans isomer] is 82:18 or more and 95:5 or less.

<16> The fragrance composition according to any of <1> to <15>, wherein the mass ratio of the cis isomer to the trans isomer [cis isomer:trans isomer] is 82:18 or more and 90:10 or less.

<17> The fragrance composition according to any of <1> to <16>, wherein the mass ratio of the cis isomer to the trans isomer [cis isomer:trans isomer] is 85:15 or more and 90:10 or less.

<18> The fragrance composition according to any of <1> to <17>, wherein $R^1$ is an alkyl group having 1 or more and 4 or less of carbon atoms.

<19> The fragrance composition according to any of <1> to <18>, wherein $R^1$ is an alkyl group having 3 or more and 4 or less of carbon atoms.

<20> The fragrance composition according to any of <1> to <19>, wherein $R^1$ is a t-butyl group.

<21> The fragrance composition according to any of <1> to <20>, wherein $R^2$ is a methyl group or an ethyl group.

<22> The fragrance composition according to any of <1> to <21>, wherein the fragrance composition further contains at least one selected from the group consisting of alcohols, phenols, esters, carbonates, aldehydes, ketones, acetals, ethers, lactones, nitriles, natural essential oils, and natural extracts that are other than the compound represented by formula (Ia), the compound represented by formula (Ib), the compound represented by formula (IIa), the compound represented by formula (IIb), the compound represented by formula (IIIa), the compound represented by formula (IIIb), the compound represented by formula (IVa), and the compound represented by formula (IVb).

<23> The fragrance composition according to any of <1> to <22>, wherein the fragrance composition further contains at least one selected from the group consisting of a lime essential oil, limonene, and menthol.

<24> The fragrance composition according to any of <1> to <23>, wherein the fragrance composition further contains at least one selected from the group consisting of Florol® (4-methyl-2-(2-methylpropyl) oxan-4-ol), hexyl acetate, and methyl dihydrojasmonate.

<25> A fragrance composition having a citrus note or a floral note, containing the fragrance composition according to any of <1> to <24>.

<26> A cosmetic, containing the fragrance composition according to any of <1> to <25>.

<27> A cleaning composition, containing the fragrance composition according to any of <1> to <25>.

<28> A method for using the fragrance composition according to any of <1> to <25> as a fragrance-imparting component.

In Reference Examples, Examples, and Comparative Examples below, "%" refers to "% by mass" unless otherwise specified. The mass of the catalyst is the mass in the dry state.

<Apparatus and Analytical Conditions for Gas Chromatography>

GC apparatus: 7890B manufactured by Agilent Technologies, Inc., hydrogen flame ionization detector Column: For a yield analysis, DB-1 (capillary column, 100% dimethylpolysiloxane, inner diameter: 0.25 mm, length: 30 m, film thickness: 0.25 μm, manufactured by Agilent Technologies, Inc.) was used. For an analysis of the cis and trans isomers, DB-WAX (capillary column, polyethylene glycol, inner diameter: 0.25 mm, length: 30 m, film thickness: 0.25 μm, manufactured by Agilent Technologies, Inc.) was used.

Carrier gas: He, 1.5 mL/min

Injection condition: 300° ° C., split ratio: 100/1

Injection amount: 1 μL

Detection condition: FID system, 300° C.

Column temperature condition: The temperature was raised from 80° C. to 300° C. at a rate of 10° C./min and maintained at 300° ° C.for 10 minutes.

REFERENCE EXAMPLE 1

Production of 1-(2-T-Butylphenyloxy)-2-Butanol (3)

[Chemical Formula 8]

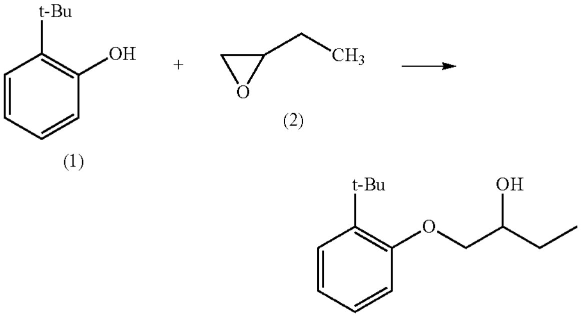

(1) (2) (3)

In a 1-liter round-bottom flask equipped with a Dimroth and a dropping funnel, 2-t-butylphenol (1) (manufactured by FUJIFILM Wako Pure Chemical Corporation, 350 g) and a 48% sodium hydroxide aqueous solution (manufactured by KANTO CHEMICAL CO., INC., 35 g) were added under nitrogen stream and heated to 80° C., to which 1,2-butylene oxide (2) (manufactured by TOKYO CHEMICAL INDUSTRY CO., LTD., 176 g) was added dropwise for about 2 hours and stirred for 5 hours at 80° C. After cooling of the reaction mixture, the organic layer was separated from the sodium hydroxide aqueous solution at the lower layer and distilled to obtain 1-(2-t-butylphenyloxy)-2-butanol (3) with a yield of 96%.

Reference Example 2

Production of 1-(2-T-Butylcyclohexyloxy)-2-Butanol (4)

[Chemical Formula 9]

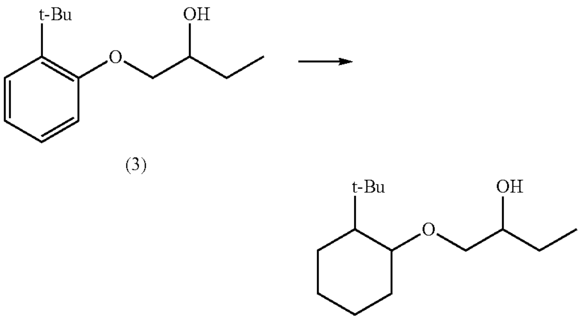

(3)

(4)

In a 500-mL autoclave, 1-(2-t-butylphenyloxy)-2-butanol (3) (250 g) obtained in Reference Example 1, an active carbon-supported palladium catalyst (manufactured by N.E. Chemcat Corporation, trade name: S-type, 50% hydrated product, supporting amount of palladium: 2%, 4.75 g) and an active carbon supported ruthenium catalyst (manufactured by N.E. Chemcat Corporation, 50% hydrated product, supporting amount of ruthenium: 5%, 0.25 g) were added and allowed to react at a hydrogen pressure of 2.0 MPa at 190° ° C. for 6 hours.

After the reaction was completed, the catalyst was filtered, and the filtrate was distilled to obtain 1-(2-t-butylcyclohexyloxy)-2-butanol (4) with a yield of 70%. The analysis of gas chromatograph of the product showed that the mass ratio of the cis isomer to the trans isomer of the product was cis:trans=57:43. The cis isomer includes a compound represented by formula (Ia-1), a compound represented by formula (Ib-1), a compound represented by formula (IIa-1), and a compound represented by formula (IIb-1). The trans isomer includes a compound represented by formula (IIIa-1), a compound represented by formula (IIIb-1), a compound represented by formula (IVa-1), and a compound represented by formula (IVb-1). The cis isomer ratio [the sum of the compound represented by formula (Ia-1) and the compound represented by formula (Ib-1): the sum of the compound represented by formula (IIa-1) and the compound represented by formula (IIb-1) (mass ratio)] was 48:52.

[Chemical Formula 10]

Cis isomer

A mixture of

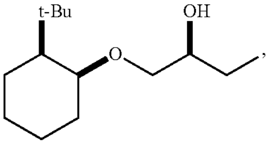

, (Ia-1)

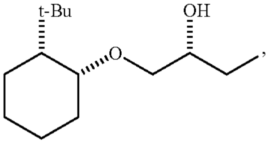

, (Ib-1)

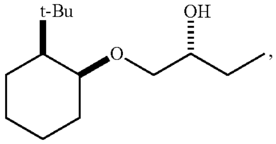

, and (IIa-1)

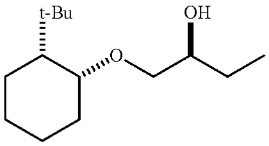 [SMILES: CC[C@H](O)CO[C@@H]1CCCC[C@@H]1C(C)(C)C]

(IIb-1)

Trans isomer

A mixture of

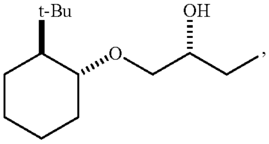

, (IIIa-1)

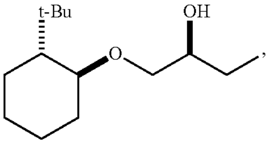

, (IIIb-1)

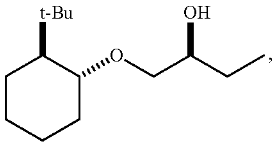

, and (IVa-1)

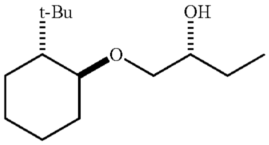 [SMILES: CC[C@@H](O)CO[C@H]1CCCC[C@@H]1C(C)(C)C]

(IVb-1)

Reference Example 3

Production of 1-(Cis-2-T-Butylcyclohexyloxy)-2-Butanol (100% Cis Isomer)

Here, 1-(cis-2-t-butylcyclohexyloxy)-2-butanol (100% cis isomer) is a mixture of the compound represented by formula (Ia-1), the compound represented by formula (Ib-1), the compound represented by formula (IIa-1), and the compound represented by formula (IIb-1).

[Chemical Formula 11]

(Ia-1)

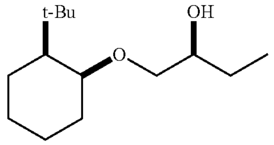

(Ib-1)

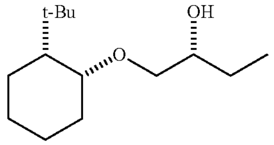

(IIa-1)

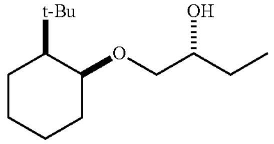

(IIb-1)

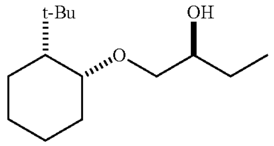

Using a 20-stage rectifier, 137 g of the mixture of the cis and trans isomers of 1-(2-t-butylcyclohexyloxy)-2-butanol obtained in Reference Example 2 was rectified at a reflux ratio of 40, yielding 8 g of 1-(cis-2-t-butylcyclohexyloxy)-2-butanol (purity: 98%, 100% cis isomer). The analysis of gas chromatograph of the product showed that the isomer ratio [the sum of the compound represented by formula (Ia-1) and the compound represented by formula (Ib-1): the sum of the compound represented by formula (IIa-1) and the compound represented by formula (IIb-1) (mass ratio)] of the 1-(cis-2-t-butylcyclohexyloxy)-2-butanol (purity: 98%, 100% cis isomer) was 70:30.

EXAMPLE 1

A fragrance composition of Example 1 was produced by adding 2.8 g of 1-(2-t-butylcyclohexyloxy)-2-butanol (cis: trans (mass ratio)=57:43) obtained in Reference Example 2 to 1 g of 1-(cis-2-t-butylcyclohexyloxy)-2-butanol (100% cis) obtained in Reference Example 3 and mixing them. The cis:trans mass ratio and the cis isomer ratio of the resultant fragrance composition were as below.

<Cis:trans mass ratio> cis:trans (mass ratio)=68:32

<Cis isomer ratio>

The mass ratio of the sum of the compound represented by formula (Ia-1) and the compound represented by formula (Ib-1) to the sum of the compound represented by formula (IIa-1) and the compound represented by formula (IIb-1) was 56.5:43.5.

EXAMPLE 2

A fragrance composition of Example 2 was produced in the same manner as in Example 1, by adding 1.3 g of 1-(2-t-butylcyclohexyloxy)-2-butanol (cis:trans (mass ratio) =57:43) obtained in Reference Example 2 to 1 g of 1-(cis-2-t-butylcyclohexyloxy)-2-butanol (100% cis) obtained in Reference Example 3 and mixing them. The cis:trans mass ratio and the cis isomer ratio of the resultant fragrance composition were as below.

<Cis:trans mass ratio> cis:trans (mass ratio)=75:25

<Cis isomer ratio>

The mass ratio of the sum of the compound represented by formula (Ia-1) and the compound represented by formula (Ib-1) to the sum of the compound represented by formula (IIa-1) and the compound represented by formula (IIb-1) was 60.6:39.4.

EXAMPLE 3

A fragrance composition of Example 3 was produced in the same manner as in Examples 1 and 2, by adding 0.8 g of 1-(2-t-butylcyclohexyloxy)-2-butanol (cis:trans (mass ratio) =57:43) obtained in Reference Example 2 to 1 g of 1-(cis-2-t-butylcyclohexyloxy)-2-butanol (100% cis) obtained in Reference Example 3 and mixing them. The cis:trans mass ratio and the cis isomer ratio of the resultant fragrance composition were as below.

<Cis:trans mass ratio> cis:trans (mass ratio)=80:20

<Cis isomer ratio>

The mass ratio of the sum of the compound represented by formula (Ia-1) and the compound represented by formula (Ib-1) to the sum of the compound represented by formula (IIa-1) and the compound represented by formula (IIb-1) was 63.1:36.9.

EXAMPLE 4

A fragrance composition of Example 4 was produced in the same manner as in Examples 1 to 3, by adding 0.5 g of 1-(2-t-butylcyclohexyloxy)-2-butanol (cis:trans mass ratio=57:43) obtained in Reference Example 2 to 1 g of 1-(cis-2-t-butylcyclohexyloxy)-2-butanol (100% cis) obtained in Reference Example 3 and mixing them. The cis:trans mass ratio and the cis isomer ratio of the resultant fragrance composition were as below.

<Cis:trans mass ratio>

<cis:trans mass ratio=85:15

<Cis isomer ratio>

The mass ratio of the sum of the compound represented by formula (Ia-1) and the compound represented by formula (Ib-1) to the sum of the compound represented by formula (IIa-1) and the compound represented by formula (IIb-1) was 65.1:34.9.

EXAMPLE 5

A fragrance composition of Example 5 was produced in the same manner as in Examples 1 to 4, by adding 0.3 g of 1-(2-t-butylcyclohexyloxy)-2-butanol (cis:trans mass ratio=57:43) obtained in Reference Example 2 to 1 g of 1-(cis-2-t-butylcyclohexyloxy)-2-butanol (100% cis) obtained in Reference Example 3 and mixing them. The cis:trans mass ratio and the cis isomer ratio of the resultant fragrance composition were as below.

<Cis:trans mass ratio> cis:trans (mass ratio)=90:10

<Cis Isomer Ratio>

The mass ratio of the sum of the compound represented by formula (Ia-1) and the compound represented by formula (Ib-1) to the sum of the compound represented by formula (IIa-1) and the compound represented by formula (IIb-1) was 66.8:33.2.

Comparative Example 1

As a fragrance composition of Comparative Example 1, 1-(2-t-butylcyclohexyloxy)-2-butanol obtained in Reference Example 2 (cis:trans (mass ratio)=57:43, cis isomer ratio: the mass ratio of the sum of the compound represented by formula (Ia-1) and the compound represented by formula (Ib-1) to the sum of the compound represented by formula (IIa-1) and the compound represented by formula (IIb-1) =48.0:52.0) was used in a sensory evaluation.

Comparative Example 2

A fragrance composition of Comparative Example 2 was produced in the same manner as in Examples 1 to 5, by adding 6.0 g of 1-(2-t-butylcyclohexyloxy)-2-butanol (cis:trans (mass ratio)=57:43) obtained in Reference Example 2 to 1 g of 1-(cis-2-t-butylcyclohexyloxy)-2-butanol (100% cis) obtained in Reference Example 3 and mixing them. The cis:trans mass ratio and the cis isomer ratio of the resultant fragrance composition were as below.

<Cis:trans mass ratio> cis:trans mass ratio=63:37

<cis isomer ratio>

The mass ratio of the sum of the compound represented by formula (Ia-1) and the compound represented by formula (Ib-1) to the sum of the compound represented by formula (IIa-1) and the compound represented by formula (IIb-1) was 53.0:47.0.

Comparative Example 3

As a fragrance composition of Comparative Example 3, 1-(cis-2-t-butylcyclohexyloxy)-2-butanol obtained in Reference Example 3 (100% cis, the mass ratio of the sum of the compound represented by formula (Ia-1) and the compound represented by formula (Ib-1) to the sum of the compound represented by formula (IIa-1) and the compound represented by formula (IIb-1)=70:30) was used in a sensory evaluation.

Sensory Evaluation

The odors of the fragrance compositions of Examples 1 to 5 and Comparative Examples 1 to 3 were evaluated by three expert panelists. In the evaluation, fragrance test strips (manufactured by Daimonji Paper Co., Ltd., 150 mm×7 mm) were used. The fragrance compositions of Examples 1 to 5 and Comparative Examples 1 to 3 having different isomer ratios were attached to the ends of the strips. After a lapse of one hour, the odors were evaluated indoors. The sensory evaluation was performed in terms of odor characteristics and intensity. The odor characteristics and intensity were relatively evaluated in five levels. A larger value is preferred.

The longevity of the fragrance compositions was judged based on the days the scent lasted. Table 1 indicates the scent lasted days. Table 1 also indicates the quality of the fragrance as a whole and the characteristics perceived by the three expert panelists in the sensory evaluation. Table 1 summarizes these results.

TABLE 1

| | Cis:trans mass ratio | Soft-ness | Freshness (Transparence) | Natural richness | Intensity | Longevity (day) | Cis isomer ratio (mass ratio)[1)] | Evaluation of fragrance (by three expert panelists) |
|---|---|---|---|---|---|---|---|---|
| Comp. Ex. 1 | 57:43 | 2 | 2 | 2 | 5 | 4 | 48.0:52.0 | The composition had amber and woody scents but lacked a soft impression. |
| Comp. Ex. 2 | 63:37 | 2 | 2 | 2 | 5 | 4 | 53.0:47.0 | The composition had amber and woody scents but lacked a soft impression. |
| Ex. 1 | 68:32 | 4 | 4 | 5 | 4 | 4 | 56.5:43.5 | A woody soft and fresh impression was intensified while the longevity was maintained. |
| Ex. 2 | 76:25 | 4 | 4 | 5 | 4 | 4 | 60.6:39.4 | A woody soft and fresh impression was intensified while the longevity was maintained. |
| Ex. 3 | 80:20 | 4 | 4 | 4 | 3 | 3 | 63.1:36.9 | A woody soft and fresh impression was intensified, but the longevity was slightly insufficient. |
| Ex. 4 | 85:15 | 5 | 5 | 4 | 3 | 3 | 65.1:34.9 | A woody soft and fresh impression was intensified, but the longevity was slightly insufficient. |
| Ex. 5 | 90:10 | 5 | 5 | 4 | 2 | 3 | 66.8:33.2 | A woody soft and fresh impression was highly intensified, but the longevity was slightly insufficient. |
| Comp. Ex. 3 | 100:0 | 5 | 5 | 3 | 2 | 2 | 70:30 | A woody soft and fresh impression was highly intensified, but the longevity was insufficient. |

[1)]The sum of the compound represented by formula (Ia-1) and the compound represented by formula (Ib-1): the sum of the compound represented by formula (IIa-1) and the compound represented by formula (IIb-1)

Ex: Example. Comp. Ex .: Comparative Example

Cis isomer (Ia-1)

A mixture of

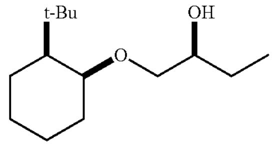

,

-continued (Ib-1)

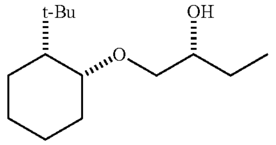

, (IIa-1)

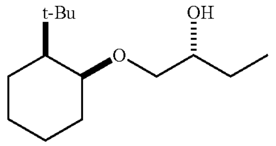

and (IIb-1)

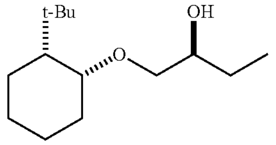

Trans isomer (IIIa-1)

A mixture of 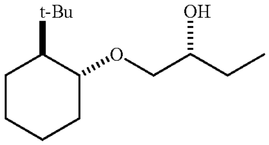 , (IIIb-1)

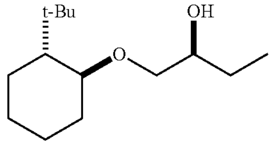

, (IVa-1)

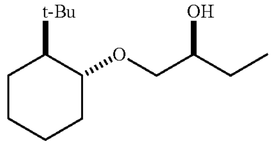

and (IVb-1)

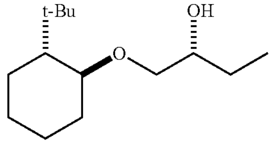

Table 1 shows that the fragrance compositions of the present invention exhibited an effect of intensifying a woody soft and fresh impression while maintaining longevity.

Formulation Example 1

The fragrance compositions of Examples 1 to 5 and Comparative Examples 1 to 3 (100 parts by weight) were each mixed with a formulated fragrance material of a citrus note (lime-sparkling note) (900 parts by mass) having the following composition to prepare compositions for sensory evaluation. Table 3 shows the results. In the evaluation results, the degree of the effect was relatively evaluated in five levels. A larger value is preferred.

TABLE 2

<Composition of the formulated fragrance material of citrus note (lime-sparkling note) >

| | |
|---|---|
| Dipropylene glycol | 17.9 parts by mass |
| Damascenone | 0.01 parts by mass |
| Ethyl acetate | 2.7 parts by mass |
| Eugenol | 36 parts by mass |
| Isoamyl acetate | 2.7 parts by mass |
| Lime essential oil | 450 parts by mass |
| Limonene | 206.1 parts by mass |
| L-menthol | 45 parts by mass |
| Orange base | 108 parts by mass |
| o-tert-Butylcyclohexyl acetate | 31.5 parts by mass |
| Tridecene-2-nitrile | 0.09 parts by mass |
| Total | 900 parts by mass |

TABLE 3

<Results of sensory evaluation>

| | Sparkling (bright impression) | Diffusibility | Evaluation of fragrance (by three expert panelists) |
|---|---|---|---|
| Comp. Ex. 1 | 2 | 1 | The composition was low in diffusibility and had no sparkling zesty bright impression. |
| Comp. Ex. 2 | 2 | 1 | The composition was low in diffusibility and had no sparkling zesty bright impression. |
| Ex. 1 | 5 | 4 | The composition had sparkling zesty brightness. |
| Ex. 2 | 6 | 5 | The composition had sparkling zesty brightness. |
| Ex. 3 | 4 | 5 | Sparkling zesty brightness was perceived, but a bit weak. |
| Ex. 4 | 4 | 4 | Sparkling zesty brightness was perceived, but a bit weak. |
| Ex. 5 | 3 | 4 | The composition had sparkling zesty brightness but a weak lingering scent. |
| Comp. Ex. 3 | 2 | 4 | The composition had sparkling zesty brightness but had no lingering scent. |

Ex.: Example,
Comp. Ex.: Comparative Example

The results of the sensory evaluation by the three expert panelists in Table 3 showed that the fragrance compositions of the present invention newly added a sparkling zesty bright impression and improved diffusibility.

Formulation Example 2

Similarly to Formulation Example 1, the fragrance compositions of Examples 1 to 5 and Comparative Examples 1 to 3 (100 parts by weight) were each mixed with a formulated fragrance material of a floral note (floral bouquet, white floral note) (900 parts by mass) having the following composition to prepare compositions for sensory evaluation. Table 5 shows the results. In the evaluation results, the degree of the effect was relatively evaluated in five levels. A larger value is preferred.

TABLE 4

<Composition of the formulated fragrance material of floral note (floral bouquet, white floral note) >

| | |
|---|---|
| Allyl cyclohexyl glycolate | 5 parts by mass |
| Benzyl acetate | 25 parts by mass |

TABLE 4-continued

| <Composition of the formulated fragrance material of floral note (floral bouquet, white floral note) > | |
|---|---|
| CALONE [1] | 0.2 parts by mass |
| CANTHOXAL [2] | 70 parts by mass |
| cis-3-Hexenol | 4 parts by mass |
| Dipropylene glycol | 89.8 parts by mass |
| Dihydroeugenol | 10 parts by mass |
| Elemi oil | 15 parts by mass |
| Florosa | 180 parts by mass |
| Hexyl acetate | 100 parts by mass |
| Hydroxycitronellal | 40 parts by mass |
| Methyl dihydrojasmonate | 280 parts by mass |
| β-Methyl naphthyl ketone | 3 parts by mass |
| para-Amylcyclohexanone | 35 parts by mass |
| Phenylethyl alcohol | 30 parts by mass |
| Styralyl acetate | 10 parts by mass |
| TRIPLAL [3] | 3 parts by mass |
| Total | 900 parts by mass |

[1] CALONE: trade name of Firmenich, 7-methyl-3,4-dihydro-2H-benzodioxepin-3-one

[2] CANTHOXAL: trade name of IFF, 2-methyl-3-(para-methoxyphenyl)-propanal

[3] TRIPLAL: trade name of IFF, 2,4-dimethyl-3-cyclohexene-1-carboxaldehyde

TABLE 5

<Results of sensory evaluation>

| | Natural richness and quality feel | Diffusibility | Evaluation of fragrance (by three expert panelists) |
|---|---|---|---|
| Comp. Ex. 1 | 2 | 1 | The composition had poor diffusibility and no natural quality feel. |
| Comp. Ex. 2 | 2 | 1 | The composition had poor diffusibility and no natural quality feel. |
| Ex. 1 | 5 | 4 | The composition had a strong natural floral feeling and gave the quality feel and a sense of luxury. |
| Ex. 2 | 5 | 5 | The composition had a strong natural floral feeling and gave the quality feel and a sense of luxury. |
| Ex. 3 | 4 | 5 | The composition had a natural floral feeling and gave the quality feel and a sense of luxury. |
| Ex. 4 | 4 | 4 | The composition had a natural floral feeling and gave the quality feel and a sense of luxury. |
| Ex. 5 | 3 | 4 | The composition had a natural floral feeling and gave the quality feel and a sense of luxury, but the longevity was slightly insufficient. |
| Comp. Ex. 3 | 2 | 4 | The composition had a natural floral feeling and gave the quality feel and a sense of luxury, but the longevity was insufficient. |

Ex.: Example, Comp. Ex.: Comparative Example

The results of the sensory evaluation by the three expert panelists showed that the fragrance compositions of the present invention had an increased floral impression and newly added the quality feel and a sense of luxury while having improved diffusibility.

The present invention provides the fragrance composition from which a woody soft and fresh impression is perceivable. Further, by blending the fragrance composition as a fragrance material with other components, a sparkling zesty impression of a top note is produced, and green and woody nuances are added together with a floral scent, giving a natural floral feeling like being in a flower shop and thus new impressions are unexceptionally created.

The invention claimed is:

1. A fragrance composition comprising a cis isomer and a trans isomer, wherein the cis isomer comprises a compound represented by formula (Ia), a compound represented by formula (Ib), a compound represented by formula (IIa), and a compound represented by formula (IIb), the trans isomer comprises a compound represented by formula (IIIa), a compound represented by formula (IIIb), a compound represented by formula (IVa), and a compound represented by formula (IVb), and a mass ratio of the cis isomer to the trans isomer [cis isomer:trans isomer] is 65:35 or more and 95:5 or less, (Ia)

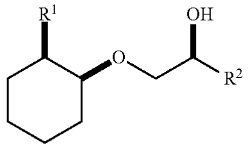

(IIa)

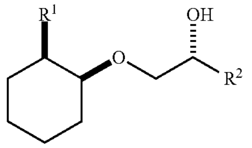

(IIIa)

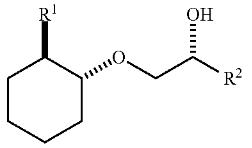

(IVa)

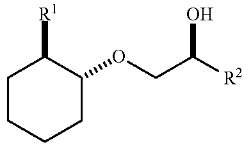

(Ib)

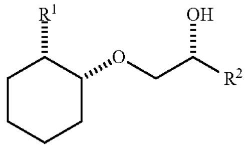

(IIb)

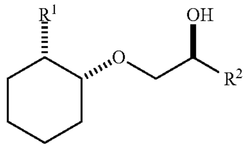

(IIIb)

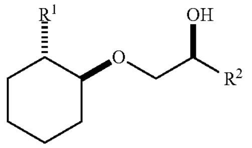

(IVb)

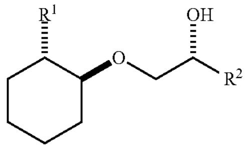

wherein in the formulae (Ia), (Ib), (IIa), (IIb), (IIIa), (IIIb), (IVa), and (IVb), $R^1$ is an alkyl group having 1 or more and 5 or less of carbon atoms, and $R^2$ is a hydrogen atom or an alkyl group having 1 or more and 4 or less of carbon atoms, wherein a mass ratio of a sum of the compound represented by formula (Ia) and the compound represented by formula (Ib) to a sum of the compound represented by formula (IIa) and the compound represented by formula (IIb) is 55:45 or more and 68:32 or less.

2. The fragrance composition according to claim 1, wherein the mass ratio of the cis isomer to the trans isomer [cis isomer:trans isomer] is 65:35 or more and 78:22 or less.

3. The fragrance composition according to claim 1, wherein the mass ratio of the cis isomer to the trans isomer [cis isomer:trans isomer] is 82:18 or more and 95:5 or less.

4. The fragrance composition according to claim 1, wherein $R^1$ is a t-butyl group.

5. The fragrance composition according to claim 1, wherein $R^2$ is a methyl group or an ethyl group.

6. The fragrance composition according to claim 1, wherein the fragrance composition further comprises at least one selected from the group consisting of alcohols, phenols, esters, carbonates, aldehydes, ketones, acetals, ethers, lactones, nitriles, natural essential oils, and natural extracts that are other than the compound represented by formula (Ia), the compound represented by formula (Ib), the compound represented by formula (IIa), the compound represented by formula (IIb), the compound represented by formula (IIIa), the compound represented by formula (IIIb), the compound represented by formula (IVa), and the compound represented by formula (IVb).

7. The fragrance composition according to claim 1, wherein the fragrance composition further comprises at least one selected from the group consisting of a lime essential oil, limonene, and menthol.

8. The fragrance composition according to claim 1, wherein the fragrance composition further comprises at least one selected from the group consisting of 4-methyl-2-(2-methylpropyl) oxan-4-ol, hexyl acetate, and methyl dihydrojasmonate.

9. The fragrance composition according to claim 1, wherein the mass ratio of the cis isomer to the trans isomer [cis isomer:trans isomer] is 68:32 or more and 90:10 or less.

10. The fragrance composition according to claim 1, wherein the mass ratio of the cis isomer to the trans isomer [cis isomer:trans isomer] is 68:32 or more and 78:22 or less.

11. The fragrance composition according to claim 1, wherein the mass ratio of the cis isomer to the trans isomer [cis isomer:trans isomer] is 68:32 or more and 75:25 or less.

12. The fragrance composition according to claim 1, wherein the mass ratio of the cis isomer to the trans isomer [cis isomer:trans isomer] is 82:18 or more and 90:10 or less.

13. The fragrance composition according to claim 1, wherein the mass ratio of the cis isomer to the trans isomer [cis isomer:trans isomer] is 85:15 or more and 90:10 or less.

14. A fragrance composition having a citrus note or a floral note, comprising the fragrance composition according to claim 1.

15. A cosmetic, comprising the fragrance composition according to claim 1.

16. A cleaning composition, comprising the fragrance composition according to claim 1.

17. A method for imparting a fragrance to a composition, comprising:

adding the fragrance composition according to claim 1 as a fragrance-imparting component to the composition.

* * * * *